United States Patent
Green et al.

(10) Patent No.: US 9,084,687 B2
(45) Date of Patent: Jul. 21, 2015

(54) ORIENTATION GUIDE

(75) Inventors: Ivan Green, Hope Valley (GB); Robert Freeman, Leeds (GB); Steven Gowers, Warsaw, IN (US)

(73) Assignee: DEPUY INTERNATIONAL LIMITED (GB)

( * ) Notice: Subject to any disclaimer, the term of this patent is extended or adjusted under 35 U.S.C. 154(b) by 663 days.

(21) Appl. No.: 13/145,357

(22) PCT Filed: Dec. 18, 2009

(86) PCT No.: PCT/GB2009/051740
§ 371 (c)(1), (2), (4) Date: Oct. 28, 2011

(87) PCT Pub. No.: WO2010/084299
PCT Pub. Date: Jul. 29, 2010

(65) Prior Publication Data
US 2012/0035612 A1    Feb. 9, 2012

(30) Foreign Application Priority Data
Jan. 20, 2009 (GB) .................................. 0900830.1

(51) Int. Cl.
*A61B 17/58* (2006.01)
*A61B 17/17* (2006.01)
(Continued)

(52) U.S. Cl.
CPC ........... *A61F 2/4657* (2013.01); *A61B 17/1746* (2013.01); *A61F 2/4603* (2013.01);
(Continued)

(58) Field of Classification Search
CPC ........................ A61B 17/1742; A61B 17/1746
USPC .......................................... 606/86 R, 96, 102
See application file for complete search history.

(56) References Cited

U.S. PATENT DOCUMENTS 1,294,710 A    2/1919  Roland
3,673,688 A *  7/1972  Garlick .......................... 33/1 SA
(Continued)

FOREIGN PATENT DOCUMENTS

DE    19651476 A1    7/1998
DE    19716781 A1    10/1998
(Continued)

OTHER PUBLICATIONS

Mittelmeier H: "Mehrdimensionales Zielgeraet Fuer Diehueftchirurgie Polydimensional Positioning Jig In Hip Surgery", Medizinisch Orthopadische Technik, Gentner Verlag. Nov. 1, 1982; pp. 150-153 vol. 102, No. 6, (Nov. 1, 1982), , Stuttgart, DE; XP000826698, ISSN: 0340-5508.
(Continued)

*Primary Examiner* — Nicholas Woodall

(57) ABSTRACT

An orientation guide comprising a housing arranged to couple to a surgical instrument. In one embodiment the orientation guide further comprises first and second indicators (22, 26). The first indicator (22) is pivotally coupled to the housing (20) such that the first indicator (22) can rotate relative to the housing (20) about a first axis (24) to maintain its angular position about the first axis (24) relative to a vertical axis irrespective of movement of the housing (20). The second indicator (26) surrounds the first indicator (22) and is pivotally coupled to the housing (20) such that the second indicator (26) can rotate relative to the housing (20) about a second axis (32) orthogonal to the first axis (24) to maintain its angular position about the second axis (32) relative to the vertical axis irrespective of movement of the housing (20). The angular position of the housing (20) about the first and second axes (24,32) is indicated by the position of the first indicator (22) relative to the second indicator (26). In a second embodiment the housing (2) comprises a cavity filled with a fluid. An indicator (4) is supported within the fluid such that the indicator (4) can rotate relative to the housing (2) about a first axis to maintain its angular position about the first axis relative to a vertical axis irrespective of movement of the housing (2). The indicator (4) comprises a marking arranged to indicate the angular position of the indicator (4) relative to the housing (2) about the first axis. The housing (2) has at least one transparent portion for viewing the marking. A measuring element (8) is coupled to the housing (2) and arranged to slide relative to the housing (2) to be aligned with the indicator marking such that the angular position of the housing (2) about the first axis can be recorded.

6 Claims, 2 Drawing Sheets

(51) Int. Cl.
    *A61F 2/34*      (2006.01)
    *A61F 2/46*      (2006.01)
    *A61F 2/30*      (2006.01)
    *A61B 19/00*     (2006.01)

(52) U.S. Cl.
    CPC . *A61B 19/46* (2013.01); *A61F 2/34* (2013.01); *A61F 2002/30471* (2013.01); *A61F 2002/30617* (2013.01); *A61F 2002/4668* (2013.01); *A61F 2002/4687* (2013.01); *A61F 2220/0091* (2013.01); *A61F 2250/0097* (2013.01)

(56) References Cited

U.S. PATENT DOCUMENTS

| | | | |
|---|---|---|---|
| 3,769,710 A | * | 11/1973 | Reister ............................ 33/320 |
| 3,956,831 A | | 5/1976 | Sibley |
| 6,302,890 B1 | | 10/2001 | Leone, Jr. |
| 2006/0184177 A1 | * | 8/2006 | Echeverri ........................ 606/91 |

FOREIGN PATENT DOCUMENTS

| | | |
|---|---|---|
| JP | 2004045190 A | 2/2004 |
| WO | WO 2005009303 A1 | 2/2005 |
| WO | WO 2005046475 A1 | 5/2005 |
| WO | WO 2005099636 A1 | 10/2005 |
| WO | WO 2008121090 A1 | 10/2008 |

OTHER PUBLICATIONS

PCT International Search Report and Written Opinion PCT/GB2009/051740 dated Jul. 21, 2010.
UK Search Report—0900830.1 dated Mar. 20, 2009.

* cited by examiner

ORIENTATION GUIDE

CROSS REFERENCE TO RELATED APPLICATION

This application is a National Stage 35 U.S.C. 371 of International Patent Application PCT/GB2009/051740 filed Dec. 18, 2009.

BACKGROUND OF THE INVENTION

The present invention relates to an orientation guide. In particular, embodiments of the present invention relate to an orientation guide that can be coupled to a surgical instrument in order to assist in correctly orientating the instrument relative to a patient.

During surgical procedures it is commonly necessary to accurately locate prostheses and instruments. For instance, during implantation of an acetabular cup into a pelvis, it is important to ensure that the cup is accurately located within a reamed cavity. Typically, such a procedure requires a number of separate instruments to be used. It is important to ensure that the alignment determined for the cup during the initial surgical steps is maintained during later surgical steps. In particular, it is important to insure that each surgical instrument is orientated correctly relative to the first used surgical instrument. For instance, the required position of an acetabular cup may be initially determined. The cavity must then be reamed. It is important that the desired varus-valgus angle of the cup is maintained during the reaming by ensuring that the reamer is orientated correctly relative to the instrument used to determine the initial position of the cup. The varus-valgus angle for a patient who is lying on a horizontal operating table such that their long axis is aligned horizontally corresponds to the inclination angle relative to a horizontal plane of a longitudinal axis of an instrument which is aligned with the axis of the cup. Preferably, any rolling movement of the instrument about its longitudinal axis should also be detected and corrected.

The varus-valgus angle must then be maintained during the implantation of the cup. Typically, the cup is coupled to an elongate instrument having an impaction surface at the opposite end. The impaction surface is subjected to an impaction force to drive the cup into the cavity. It is possible that the varus-valgus angle could drift during the impaction.

WO-2005/009303 discloses an orientation device for a surgical instrument. The orientation device may be used for orientating a surgical instrument during the implantation of a surgical cup. A frame is provided which couples to a surgical instrument. The frame includes a spirit level, in particular a bull's-eye spirit level, which is arranged to indicate when the spirit level is lying in a horizontal plane by a bubble being positioned within an inner circle. The frame is flexible such then when the instrument is in a required orientation the frame can be deformed until the spirit level lies in a horizontal plane. Further movement of the instrument causing the orientation of the instrument to change (either through rolling motion about the longitudinal axis of the instrument or through a change in the inclination of the instrument) is detectable by observing the position of the bubble within the spirit level.

However, spirit levels lack sensitivity to angular movement beyond a limited preset angular range. In general, spirit levels, including bull's-eye spirit levels are only able to indicate whether they are positioned horizontally and not indicate the magnitude of any difference from the horizontal.

BRIEF SUMMARY OF THE INVENTION

It is an object of embodiments of the present invention to obviate or mitigate one or more of the problems associated with the prior art, whether identified herein or elsewhere. In particular, it is an object of embodiments of the present invention to provide an orientation guide which can be coupled to a surgical instrument used during the implantation of an acetabular cup to indicate angular movement (that is, a change in the orientation) of the instrument and to provide for measurement of the angular movement.

According to a first aspect of the present invention there is provided an orientation guide comprising: a housing arranged to couple to a surgical instrument; a first indicator pivotally coupled to the housing such that the first indicator can rotate relative to the housing about a first axis to maintain its angular position about the first axis relative to a vertical axis irrespective of movement of the housing; and a second indicator surrounding the first indicator and pivotally coupled to the housing such that the second indicator can rotate relative to the housing about a second axis orthogonal to the first axis to maintain its angular position about the second axis relative to the vertical axis irrespective of movement of the housing; wherein the angular position of the housing about the first and second axes is indicated by the position of the first indicator relative to the second indicator.

An advantage of the first aspect of the present invention is that angular movement of a surgical instrument may be detected and measured. Specifically, when the instrument is used during the implantation of an acetabular cup, the varus-valgus angle of the instrument may be measured. The orientation guide may be used to measure the orientation of a first instrument. The guide may then be transferred to a second instrument and used to orientate a second instrument to the same orientation as the first instrument. This may be particularly advantageous during surgical procedures in order to preserve orientation information set for a first instrument during a multiple stage surgical procedure.

The first and second indicators may be weighted such that they maintain their angular position about their respective axis relative to the vertical axis irrespective of movement of the housing.

At least one of the first and second indicators may comprise a gauge such that the position of the first indicator relative to the second indicator about at least one of the first and second axes can be measured.

The first indicator may comprise a first ring. The second indicator may comprise a second ring surrounding the first ring. The housing may comprise a third ring surrounding the second ring, the first, second and third rings being arranged concentrically. The angular position of the housing about the first and second axes may be indicated by the position around the first and second rings where the rings cross.

The second ring may comprises a gauge extending around the circumference of the ring and the first ring comprises a first alignment mark, the angular position of the housing about the first axis being indicated by the position of the first alignment mark relative to the gauge. The first ring may further comprise second and third alignment marks, the angular position of the housing about the second axis being indicated by the position of the second ring relative to the second and third alignment marks. A first predetermined angular position of the housing about the second axis may be indicated by the second ring being located between the second and third alignment marks.

According to a second aspect of the present invention there is provided a method of orientating a surgical instrument, the method comprising: coupling a housing of an orientation guide to a surgical instrument, the orientation guide further comprising a first indicator pivotally coupled to the housing such that the first indicator can rotate relative to the housing about a first axis to maintain its angular position about the first axis relative to a vertical axis irrespective of movement of the housing, and a second indicator surrounding the first indicator and pivotally coupled to the housing such that the second indicator can rotate relative to the housing about a second axis orthogonal to the first axis to maintain its angular position about the second axis relative to the vertical axis irrespective of movement of the housing; and rotating the surgical instrument about the first and second axes until the first indicator is in a predetermined position relative to the second indicator.

According to a third aspect of the present invention there is provided a method of orientating a surgical instrument, the method comprising: coupling a housing of an orientation guide to a surgical instrument, the orientation guide further comprising a first indicator pivotally coupled to the housing such that the first indicator can rotate relative to the housing about a first axis to maintain its angular position about the first axis relative to a vertical axis irrespective of movement of the housing, and a second indicator surrounding the first indicator and pivotally coupled to the housing such that the second indicator can rotate relative to the housing about a second axis orthogonal to the first axis to maintain its angular position about the second axis relative to the vertical axis irrespective of movement of the housing; rotating the surgical instrument about the first and second axes until the surgical instrument is in a predetermined orientation; and recording the position of the first indicator relative to the second indicator; wherein the instrument can later be repositioned in the predetermined orientation by rotating the instrument about the first and second axes until the first indicator is in the same recorded position relative to the second indicator.

According to a fourth aspect of the present invention there is provided an orientation guide comprising: a housing arranged to couple to a surgical instrument, the housing comprising a cavity filled with a fluid; an indicator supported within the fluid such that the indicator can rotate relative to the housing about a first axis to maintain its angular position about the first axis relative to a vertical axis irrespective of movement of the housing, the indicator comprising a marking arranged to indicate the angular position of the indicator relative to the housing about the first axis, the housing having at least one transparent portion for viewing the marking; and a measuring element coupled to the housing and arranged to slide relative to the housing to be aligned with the indicator marking such that the angular position of the housing about the first axis can be recorded.

The indicator may comprise a body supported by the fluid and arranged to rotate within the housing. The housing may comprise a hollow, substantially spherical ball, the indicator being weighted such that it floats within the fluid in a predetermined orientation relative to a horizontal plane.

The indicator may be magnetic such that it is arranged to align itself with the Earth's magnetic field or there may be a magnet coupled to the indicator such that the magnet can rotate relative to the indicator to align itself with the Earth's magnetic field.

The indicator marking may comprise a ring extending around the indicator arranged such that when the indicator is floating in its predetermined orientation the ring lies in a horizontal plane, and wherein the measuring element comprises an elongate element extending around at least part of the spherical housing and coupled to the housing so that it can slide around the housing to be aligned with the ring to record the position of the indicator with respect to the housing.

The measuring element may be C shaped, the measuring element being coupled to a rail extending around at least part of the housing such that the recording element can slide along the rail and rotate relative to the rail to be aligned with the indicator ring, the recording means further comprising locking means for securing the position of the recording element relative to the rail.

The measuring element may be coupled to the housing along rails extending at least partially around the housing and arranged to slide along the rails, the rails incorporating alignment marks such that the angular position of the indicator relative to the housing about the first axis is indicated by the position of an indicator alignment mark relative to the rails.

According to a fifth aspect of the present invention there is provided a method of orientating a surgical instrument, the method comprising: coupling a housing of an orientation guide to a surgical instrument, the housing comprising a cavity filled with a fluid and the orientation guide further comprising an indicator supported within the fluid such that the indicator can rotate relative to the housing about a first axis to maintain its angular position about the first axis relative to a vertical axis irrespective of movement of the housing, the indicator comprising a marking arranged to indicate the angular position of the indicator relative to the housing about the first axis, the housing having at least one transparent portion for viewing the marking, and a measuring element coupled to the housing and arranged to slide relative to the housing to be aligned with the indicator marking such that the angular position of the housing about the first axis can be recorded; and rotating the surgical instrument about the first axis until the indicator marking is in a predetermined position relative to the measuring element.

According to a sixth aspect of the present invention there is provided a method of orientating a surgical instrument, the method comprising: coupling a housing of an orientation guide to a surgical instrument, the housing comprising a cavity filled with a fluid and the orientation guide further comprising an indicator supported within the fluid such that the indicator can rotate relative to the housing about a first axis to maintain its angular position about the first axis relative to a vertical axis irrespective of movement of the housing, the indicator comprising a marking arranged to indicate the angular position of the indicator relative to the housing about the first axis, the housing having at least one transparent portion for viewing the marking, and a measuring element coupled to the housing and arranged to slide relative to the housing to be aligned with the indicator marking such that the angular position of the housing about the first axis can be recorded; rotating the surgical instrument about the first axis until the surgical instrument is in a predetermined orientation; and recording the position of the indicator marking relative to the measuring element; wherein the instrument can later be repositioned in the predetermined orientation by rotating the instrument about the first axis until the indicator marking is in the same recorded position relative to the measuring element.

According to an embodiment of the invention there is provided an orientation guide comprising: a housing arranged to couple to a surgical instrument; an indicator coupled to the housing such that the indicator can rotate relative to the housing about a first axis to maintain its angular position about the first axis relative to a vertical axis irrespective of movement of the housing; and measuring means coupled to the housing such that angular movement of the indicator relative to the housing about the first axis can be measured.

The present invention will now be described, by way of example only, with reference to the accompanying drawings, in which:

DETAILED DESCRIPTION OF THE INVENTION

Figure 1:
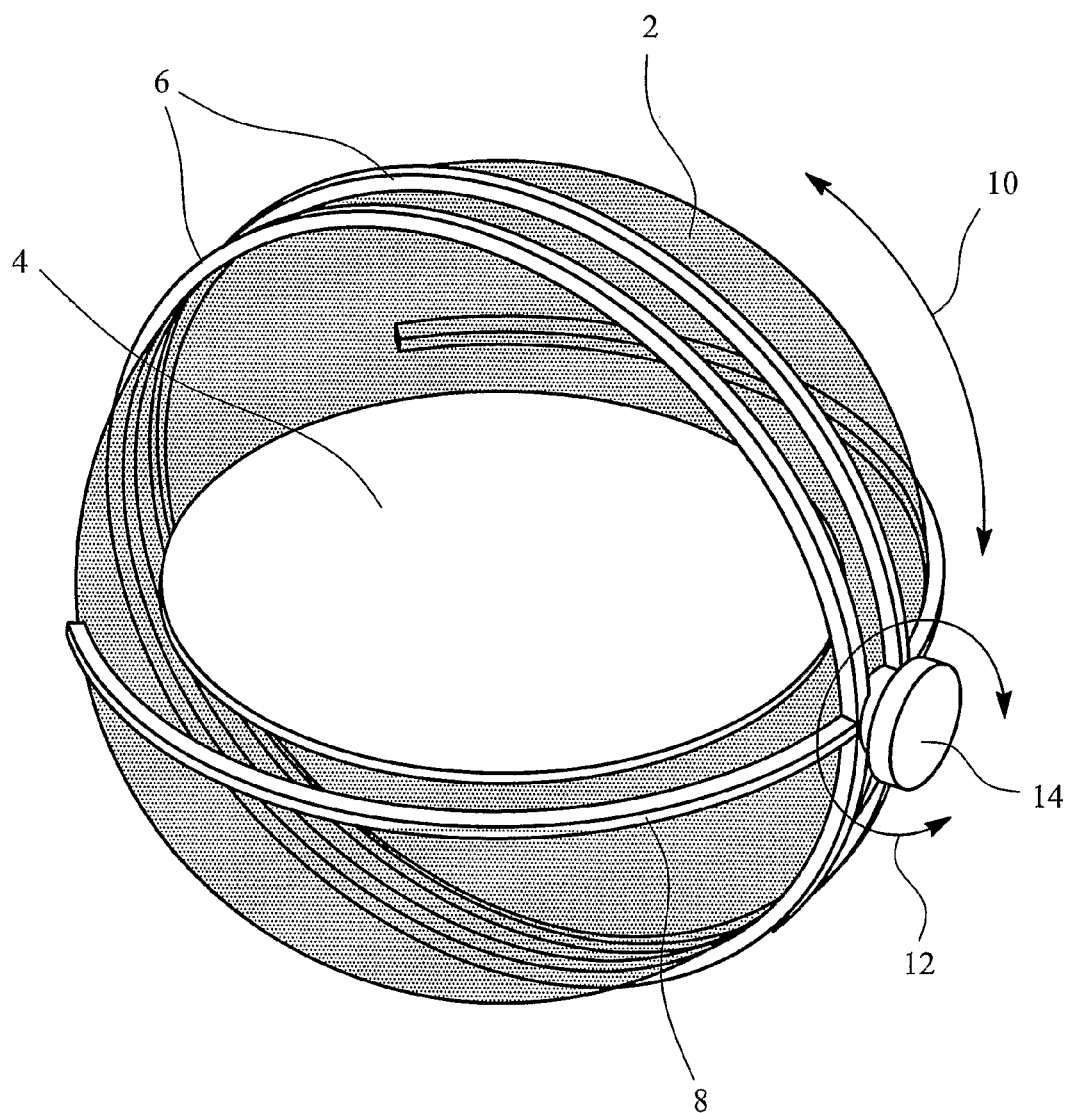
FIG. 1 schematically illustrates an orientation guide according to a first embodiment of the present invention.

Referring first to FIG. 1, this schematically illustrates an orientation guide in accordance with a first embodiment of the present invention. The orientation guide is suitable for use during a surgical procedure for recording orientation information for a first instrument and transferring this information to a second instrument. Alternatively, the orientation guide may be used to measure the orientation of an instrument. The orientation guide may be coupled to instruments used during the implantation of a prosthetic acetabular cup. It is important to ensure that each surgical instrument is orientated the same way relative to one another during implantation of an acetabular cup in order to prevent misalignment and minimise wear of the cup. The orientation information can be used to ensure that each successive instrument is correctly aligned. In particular, it is important to ensure that the varus-valgus angle is the same for each instrument.

The orientation guide comprises a transparent, hollow sphere, schematically represented by the hashed circle 2. The hollow sphere forms a housing. The hollow sphere 2 is filled with a fluid, for instance a saline solution. Floating within the sphere 2 is an indicator 4, such as a solid sphere. The indicator is weighted such that it floats in a predetermined orientation. That is, the indicator remains in a constant orientation relative to a horizontal plane (schematically illustrated by disc 4). The indicator 4 comprises alignment markings. For instance if the indicator is a sphere, a ring extends around the sphere aligned with the horizontal plane, such that if the orientation of the transparent sphere 2 changes this is visible as relative movement between the ring around the floating sphere indicator 4 and the transparent sphere 2.

The orientation guide further comprises a coupling (not shown in FIG. 1) for coupling the housing 2 to an instrument. The coupling may be entirely conventional, for instance a threaded joint, press fit connection or similar, and so will not be further described here. If the instrument changes its orientation, for instance a change in inclination of the longitudinal axis of the instrument relative to a horizontal plane or rolling about the longitudinal axis of the instrument, the indicator 4 changes position relative to the housing 2. More specifically, as the housing 2 moves, the indicator 4 maintains its previous orientation relative to the horizontal plane (for instance, due to the weighting of the sphere, the ring extending around the sphere stays aligned with the horizontal plane).

In order to measure and record the relative movement between the housing 2 and the indicator 4, the orientation guide further comprises measuring means in the form of a rail or a pair of rails 6 extending around at least part of the housing 2. Slidably and rotatably coupled to the rails 6 is a C shaped recording element 8 extending around at least part of the housing 2. The position of the indicator 4 relative to the housing 2 (that is, the position of the horizontal plane indicated by the alignment marking relative to the housing 2) may be recorded by sliding the recording element 8 along the rails 6 in either direction indicated by arrow 10 and/or rotating the recording element 8 relative to the rails in either direction indicated by arrow 12. The recording element 8 is aligned with the horizontal plane marking on the indicator 4. The recording element 8 may then be locked in position relative to the rails 6 by tightening thumb screw 14. The recording element may thus be set for two orthogonal planes of movement of the instrument: roll of the instrument about its longitudinal axis and pitching of the instrument. The rails 6 may comprise a gauge coupled to the housing 2 for measuring the absolute inclination of the instrument. Alternatively, the rails 6 may be used only for measuring the relative inclination of the instrument for transferring this information to another instrument. Pitching of the instrument represents a change in the varus-valgus angle when the orientation guide is coupled to an instrument used in the implantation of an acetabular cup such that the longitudinal axis of the instrument and the rails 6 lie in the same plane.

For the exemplary application of the present invention during implantation of an acetabular cup, when a patient is positioned on their side upon an operating table, pitching of the instrument represents a change in the varus-valgus angle of the cup. Rolling of the instrument about its longitudinal axis corresponds to rotation of the cup within the reamed acetabulum.

It is also desirable to be able to record the version angle (corresponding to a rotation of the instrument about a vertical axis). A change in the version angle corresponds to rotation of the instrument about an axis, which is normal to the horizontal plane. That is, as the instrument rotates within the horizontal plane, housing 2 also rotates. However, indicator sphere 4 floats within housing 2 and so can assume any orientation about an axis normal to the horizontal plane. In certain embodiments, the indicator 4 may be magnetic or may have a magnet coupled to it. For instance, the indicator 4 may comprise a magnetic sphere floating within housing 2. The magnet will align with the Earth's magnetic field and will stay aligned while the instrument and the housing 2 move. When the orientation guide is first coupled to an instrument for aligning the acetabular cup, the alignment of the magnet relative to the housing 2 can be recorded. Subsequently, when the orientation guide is coupled to a new instrument, the instrument can be rotated within the horizontal plane until the magnet is aligned with the same part of housing 2.

Once the orientation of the indicator 4 relative to the housing 2 has been recorded for a first instrument, the housing 2 may then be coupled to successive instruments and the orientation of the instrument adjusted until the recording element 8 is aligned with the markings upon the indicator 4.

Figure 2:
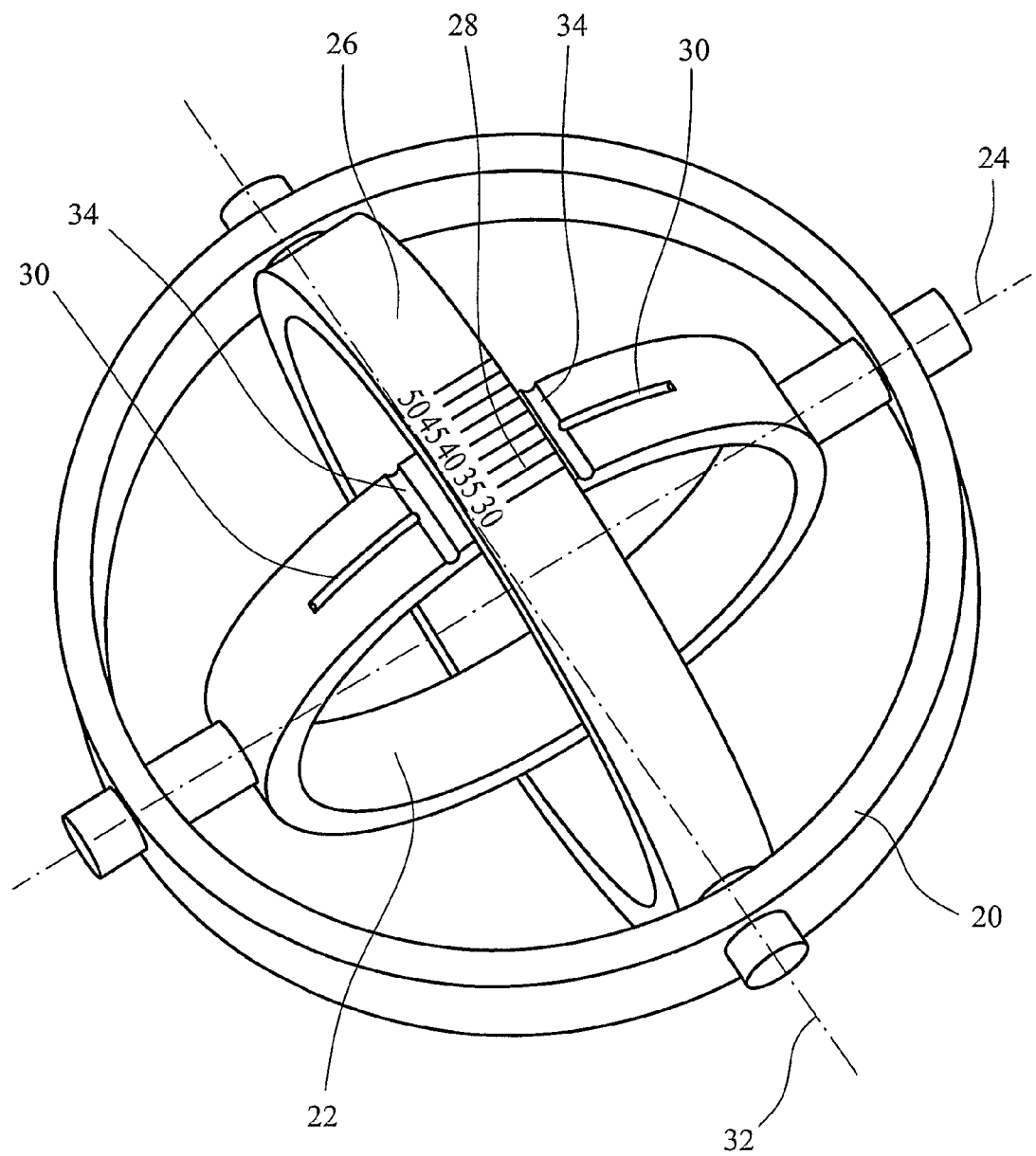
FIG. 2 schematically illustrates an orientation guide according to a second embodiment of the present invention

Referring now to FIG. 2, this schematically illustrates an orientation guide in accordance with a second embodiment of the present invention. The orientation guide of FIG. 2 comprises a mechanical orientation guide. The housing comprises an outer ring 20. As for FIG. 1, the orientation guide further comprises a coupling means (not shown) for coupling the housing ring 20 to an instrument.

The orientation guide of FIG. 2 further comprises a first indicator formed as an inner indicator ring 22 which is pivotally coupled to the housing ring 20 such that it can rotate relative to the housing ring about a first axis 24. A second indicator in the form of a gauge 26 is coupled to the housing 22 such that angular movement of the indicator ring 22 relative to the housing 20 may be measured. The gauge 26 incorporates calibrated markings 28 to allow the actual angular position of the indicator to be measured by reference to an alignment mark 30 on the indicator 22. The gauge 26 may be fixed to the housing 20. Alternatively, as illustrated in FIG. 2, the gauge 26 may be pivotally coupled to the housing 20 such that it can rotate relative to the housing 20 about a second axis 32, which is orthogonal to the first axis 24. Angular movement of the gauge ring 26 relative to the housing 20 about the second axis 32 is indicated by movement of the gauge ring 26 relative to alignment marks 34 on the indicator ring 22.

When the orientation guide of FIG. 2 is coupled to an instrument for implanting an acetabular cup such that the gauge ring 26 and the longitudinal axis of the instrument lie in the same plane, pitching of the instrument (corresponding to a change in the varus-valgus angle of the cup) is indicated by movement of the indicator ring 22 relative to the housing 20 about axis 24 and is measurable with reference to the gauge markings 28 on the gauge ring 26. Rotation of the instrument (corresponding to rotation of the cup) is detectable by movement of gauge ring 26 relative to the alignment marks 34 on the indicator ring 22. To ensure a neutral rotational position of the cup, the orientation guide should be coupled to the instrument such that the gauge ring 26 is positioned between alignment marks 34 on the indicator ring 22 when the cup which is coupled to the instrument is in the correct rotational position. The coupling of the orientation guide to the instrument should be such that the varus-valgus angle indicated by the calibration marks 28 correspond to the actual varus-valgus angle of the instrument (and hence the implanted cup).

Preferably the indicator ring 22 is weighted such that the alignment marks 30 and 34 are uppermost (that is, the indicator ring 22 lies in a vertical plane). Similarly, preferably the gauge ring 26 is weighted so that is lies in a vertical plane so as to allow the gauge ring 26 to lie within alignment marks 34 when the instrument is in a neutral angular position about the longitudinal axis of the instrument (neutral roll).

For the exemplary application of the present invention during implantation of an acetabular cup, when a patient is positioned on their side upon an operating table, pitching of the instrument represents a change in the varus-valgus angle of the cup. Rolling of the instrument about its longitudinal axis corresponds to rotation of the cup within the reamed acetabulum. Both pitching and rolling of the instrument result in a measurable shift in the point at which indicator ring 22 and gauge ring 26 cross.

Further modifications to, and applications of, the present invention will be readily apparent to the skilled person from the teaching herein, without departing from the scope of the appended claims.

The invention claimed is:

1. An orientation guide comprising:
a housing arranged to couple to a surgical instrument;
a first ring pivotally coupled to the housing such that the first ring can rotate relative to the housing about a first axis to maintain its angular position about the first axis relative to a vertical axis irrespective of movement of the housing; and
a second ring surrounding the first ring and pivotally coupled to the housing such that the second ring can rotate relative to the housing about a second axis orthogonal to the first axis to maintain its angular position about the second axis relative to the vertical axis irrespective of movement of the housing;
wherein the first and second rings are weighted such that they maintain their angular position about their respective axes relative to the vertical axis irrespective of movement of the housing; and
wherein the angular position of the housing about the first and second axes is indicated by the position of the first ring and the second ring where the rings cross.

2. The orientation guide of claim 1, wherein at least one of the first and second rings comprise a gauge such that the position of the first indicator relative to the second indicator about at least one of the first and second axes can be measured.

3. The orientation guide of claim 1, wherein the housing comprises a third ring surrounding the second ring, the first, second and third rings being arranged concentrically.

4. The orientation guide of claim 1, wherein the second ring comprises a gauge extending around the circumference of the ring and the first ring comprises a first alignment mark, the angular position of the housing about the first axis being indicated by the position of the first alignment mark relative to the gauge.

5. The orientation guide of claim 1, wherein the first ring further comprises second and third alignment marks, the angular position of the housing about the second axis being indicated by the position of the second ring relative to the second and third alignment marks.

6. The orientation guide of claim 5, wherein a first predetermined angular position of the housing about the second axis is indicated by the second ring being located between the second and third alignment marks.

* * * * *